(12) United States Patent
Sehnert et al.

(10) Patent No.: US 11,432,789 B2
(45) Date of Patent: *Sep. 6, 2022

(54) SELF-CALIBRATING TECHNIQUE FOR X-RAY IMAGING SCANNERS

(71) Applicant: CARESTREAM HEALTH, INC., Rochester, NY (US)

(72) Inventors: William J. Sehnert, Fairport, NY (US); Yuan Lin, Cupertino, CA (US); Levon O. Vogelsang, Webster, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/115,869

(22) Filed: Dec. 9, 2020

(65) Prior Publication Data

US 2021/0113176 A1 Apr. 22, 2021

Related U.S. Application Data

(63) Continuation-in-part of application No. 17/082,080, filed on Oct. 28, 2020, which is a continuation of
(Continued)

(51) Int. Cl.
*A61B 6/00* (2006.01)
*A61B 6/03* (2006.01)
(Continued)

(52) U.S. Cl.
CPC .............. *A61B 6/582* (2013.01); *A61B 6/025* (2013.01); *A61B 6/032* (2013.01); *A61B 6/06* (2013.01);
(Continued)

(58) Field of Classification Search
CPC ....... A61B 6/025; A61B 6/032; A61B 6/0421; A61B 6/06; A61B 6/08; A61B 6/4405; A61B 6/5205; A61B 6/547; A61B 6/582; A61B 6/584; A61B 6/588; A61B 90/39; A61B 90/3966
See application file for complete search history.

(56) References Cited

U.S. PATENT DOCUMENTS 8,821,017 B2 9/2014 Lalena et al.
10,517,561 B2 12/2019 Lin et al.
(Continued)

FOREIGN PATENT DOCUMENTS

WO 2016/003957 A2 1/2016

OTHER PUBLICATIONS

S. Ouadah et al., Self-Calibration of Cone-Beam CT Geometry Using 3D-2D Image Registration, *Phys. Med. Biol.*, 61, 2016, pp. 2613-2632.
(Continued)

*Primary Examiner* — Mark R Gaworecki

(57) ABSTRACT

A mobile radiography apparatus includes radiopaque markers disposed in a radiation path that extends from an x-ray source to a digital radiographic detector, which detector is mechanically uncoupled from the x-ray source or x-ray sources. A processing system calculates a position of the detector relative to the x-ray source or x-ray sources according to identified marker positions in acquired x-ray projection images, and reconstructs a volume image according to the acquired x-ray projection images.

19 Claims, 18 Drawing Sheets

Related U.S. Application Data application No. 16/692,362, filed on Nov. 22, 2019, now Pat. No. 10,842,462, which is a continuation of application No. 15/971,213, filed on May 4, 2018, now Pat. No. 10,517,561.

(60) Provisional application No. 62/598,519, filed on Dec. 14, 2017, provisional application No. 62/507,288, filed on May 17, 2017.

(51) Int. Cl.

| | | |
|---|---|---|
| *A61B 6/06* | (2006.01) | |
| *A61B 6/08* | (2006.01) | |
| *A61B 90/00* | (2016.01) | |
| *A61B 6/02* | (2006.01) | |
| *A61B 6/04* | (2006.01) | |

(52) U.S. Cl.
CPC .............. *A61B 6/08* (2013.01); *A61B 6/4405* (2013.01); *A61B 6/5205* (2013.01); *A61B 6/547* (2013.01); *A61B 6/584* (2013.01); *A61B 6/588* (2013.01); *A61B 90/39* (2016.02); *A61B 6/0421* (2013.01); *A61B 2090/3966* (2016.02)

(56) References Cited

U.S. PATENT DOCUMENTS

| | | | |
|---|---|---|---|
| 10,743,822 B2 | 8/2020 | Simon et al. | |
| 10,842,462 B2 | 11/2020 | Sehnert et al. | |
| 2006/0039591 A1 | 2/2006 | Zettel et al. | |
| 2008/0095302 A1 | 4/2008 | Ruhrnschopf et al. | |
| 2011/0191084 A1 | 8/2011 | Cooke | |
| 2015/0043712 A1 | 2/2015 | Wang et al. | |
| 2016/0174915 A1 | 6/2016 | O'Dea et al. | |
| 2016/0278732 A1 | 9/2016 | Amiri | |
| 2018/0333131 A1 | 11/2018 | Lin | |
| 2020/0000426 A1 | 1/2020 | Simon et al. | |
| 2021/0106304 A1 | 4/2021 | Sehnert et al. | |
| 2021/0177371 A1 | 6/2021 | Wang et al. | |

OTHER PUBLICATIONS

Yuan Lin and Ehsan Samei, "A fast poly-energetic iterative FBP algorithm," Physics in Medicine and Biology 59, 2014, pp. 1655-1678.

Yuan Lin and Ehsan Samei, "An efficient polyenergetic SART (pSART) reconstruction algorithm for quantitative myocardial CT perfusion," Medical Physics, 41(2), Feb. 2014, pp. 021911-1—021911-14.

F. Edward Boas and Dominik Fleischmann, "CT artifacts: Causes and reduction techniques," Imaging Med. (2012), 4(2), pp. 229-240.

Donghoon Lee et al., "Restoration of Full Data from Sparse Data in Low-Dose Chest Digital Tomosynthesis Using Deep Convolutional Neural Networks," Journal of Digital Imaging, vol. 32, No. 3, Sep. 20, 2018, pp. 489-498.

International Search Report dated Apr. 30, 2021 for International Application No. PCT/US2021/0138879, 2 pages.

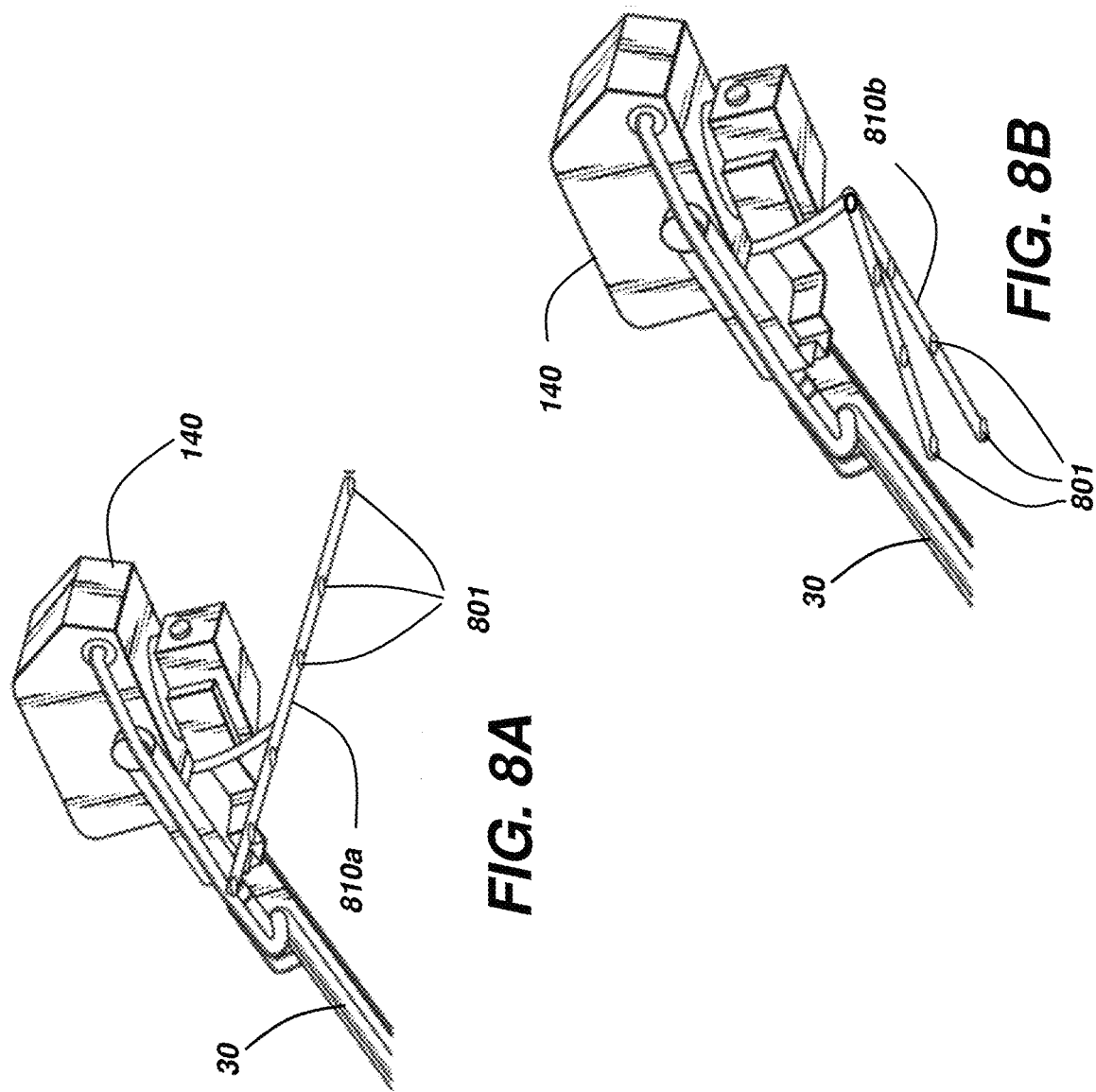

SELF-CALIBRATING TECHNIQUE FOR X-RAY IMAGING SCANNERS

CROSS REFERENCE TO RELATED APPLICATIONS

This patent application is a continuation-in-part patent application of U.S. patent application Ser. No. 17/082,080, filed on Oct. 28, 2020, entitled SELF-CALIBRATING TECHNIQUE FOR X-RAY IMAGING SCANNERS, in the name of Sehnert, et al., which is a continuation patent application of U.S. patent application Ser. No. 16/692,362, filed on Nov. 22, 2019, entitled SELF-CALIBRATING TECHNIQUE FOR X-RAY IMAGING SCANNERS, in the name of Lin, et al., which is a continuation patent application of U.S. patent application Ser. No. 15/971,213, filed on May 4, 2018, entitled SELF-CALIBRATING TECHNIQUE FOR X-RAY IMAGING SCANNERS, in the name of Lin, et al., which claims the benefit of U.S. Provisional Application U.S. Ser. No. 62/507,288, provisionally filed on May 17, 2017, entitled SELF-CALIBRATING TECHNIQUE FOR X-RAY IMAGING SCANNERS, in the name of Lin et al., and U.S. Provisional Application U.S. Ser. No. 62/598,519, provisionally filed on Dec. 14, 2017, entitled SELF-CALIBRATING TECHNIQUE FOR X-RAY IMAGING SCANNERS, in the names of Lin et al., which are both hereby incorporated herein by reference in their entirety.

TECHNICAL FIELD

The disclosure relates generally to the field of medical imaging, and in particular to a mobile radiographic imaging apparatus. More particularly, this disclosure relates to a simple and reliable self-calibrating technique for mobile X-ray imaging scanners.

BACKGROUND

Digital X-ray tomosynthesis is an imaging technique that enables three-dimensional imaging of a patient using a large-area digital detector typically used for conventional (single projection) radiography. A finite number of projection images over a limited angular range, typically between 20° and 40°, are acquired by varying the relative orientations of the x-ray tube, or x-ray source, patient and detector, typically a digital radiographic (DR) detector. This is usually accomplished by either moving both the detector and x-ray source or by fixing the position of the detector, or source, and moving the x-ray source, or detector, respectively. Three-dimensional data is reconstructed from the captured projections and may be displayed in the form of any number of slices through the patient anatomy, each parallel to the detector plane. A consequence of limited angular scanning is that the in-depth resolution is lower than the in-plane resolution of the reconstructed object.

Reconstruction of volumetric data, or 3D x-ray images, from a tomosynthesis system requires knowledge of the underlying capture geometry, including the orientation and spatial position of the detector relative to the x-ray source, the movement and position of the source relative to the detector, and potential patient motion. Precise geometric information of the imaging system (orientation of the X-ray detector, and relative locations of the X-ray tube head with respect to the X-ray detector during 2D projection image acquisition) affect the image quality of the reconstructed volume images. Mismapping between object space and the acquired 2D projection images can degrade spatial resolution and lead to image artifacts, such as ring artifacts.

In a conventional tomosynthesis system, many of the geometric variables are known, as the detector position is precisely specified and the relationship between source and detector is also well established. For stationary imaging scanners, acquisition geometry is fixed by the mechanical coupling of source and detector, such in a C-arm configuration or other type of gantry arrangement. Calibration of this geometry is straightforward, using a calibration phantom prior to image acquisition.

For a bed-side tomosynthesis system using mobile radiography apparatus, however, the detector is mechanically uncoupled from the source. Thus, the capture geometry is not fixed by system mechanics and can be difficult to determine with the desired accuracy. Mobile x-ray imaging scanners used for tomosynthesis are designed for seriously ill patients who cannot be transported to, walk to, or stand in front of, stationary imaging scanners having fixed geometry. Instead, in order to image these patients, the detector is often manually positioned under the bed-ridden patient. In this acquisition environment, without the benefit of mechanically fixed source-to-detector geometry, other approaches are needed in order to accurately determine the geometry information in real time.

There is a need for a calibration utility that is suited to estimate the geometry of a mobile radiography system used for tomosynthesis or other 3D volume imaging and that overcomes the aforementioned limitations.

SUMMARY

An aspect of the present application is to advance the art of radiography 3D volume imaging. Another aspect of this disclosure to address in whole or in part, at least the foregoing and other deficiencies in the related art. It is another aspect of this application to provide in whole or in part, at least the advantages described herein.

Another aspect of the application is to provide methods and/or apparatus by which mobile radiography carts can additionally provide 3D imaging capabilities with more accurate source/detector calibration.

Another aspect of the application is to provide methods and/or apparatus embodiments by which mobile radiography carts can acquire projection images and generate the reconstruction of three-dimensional tomographic and tomosynthesis images.

Another aspect of the application is to provide methods and/or apparatus embodiments by which mobile radiography carts can acquire x-ray 2D projection images and generate the reconstruction of two-dimensional or three-dimensional volume images, where an imaging geometry of x-ray source positions to a radiographic detection array is not known beforehand.

These objects are given only by way of illustrative example, and such objects may be exemplary of one or more embodiments of the invention. Other desirable objectives and advantages inherently achieved by the method and apparatus described herein may occur or become apparent to those skilled in the art. The invention is defined by the appended claims.

According to one aspect of the disclosure, there is provided a mobile radiography apparatus comprising a plurality of x-ray sources and a digital radiographic detector mechanically uncoupled from the x-ray sources. A plurality of radiopaque markers is disposed in one or more radiation paths each extending from one of the x-ray sources to the radiographic detector. A processor is programmed to calculate a position of the detector relative to one or more of the plurality of x-ray sources according to positions of the radio-opaque markers in x-ray projection images captured by the digital radiographic detector.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIGS. 8A-8E illustrate arrangements of cold cathode or carbon nanotube x-ray sources configured to be secured to a tube head.

DETAILED DESCRIPTION OF THE EMBODIMENTS

Figure 1:
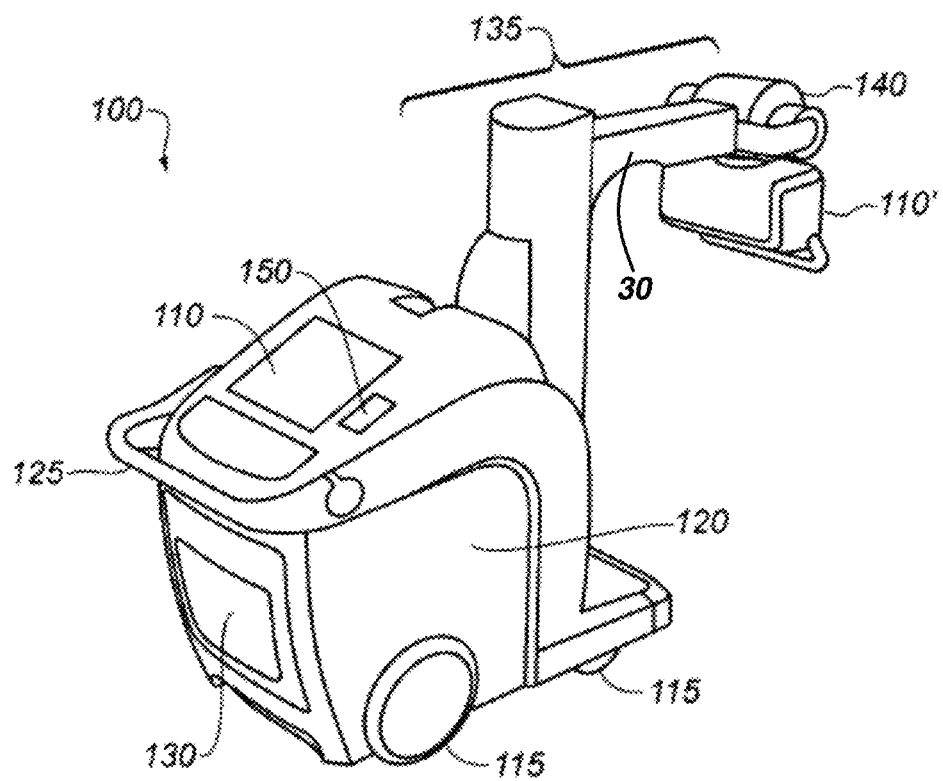
FIG. 1 is a diagram that shows a perspective view of one embodiment of a mobile radiography unit for use as a portable imaging system for tomosynthesis or other volume imaging.

The following is a description of exemplary embodiments of the invention, reference being made to the drawings in which the same reference numerals identify the same elements of structure in each of the several figures. Where they are used, the terms "first", "second", and so on, do not necessarily denote any ordinal or priority relation, but may be used for more clearly distinguishing one element or time interval from another.

Portable radiographic systems are routinely used in hospitals. Compared to standard projection radiography, volume imaging apparatus such as tomosynthesis apparatus provide improved depiction of fine details not visible in normal radiographs due to overlying structures. These benefits provide an impetus to develop portable volume imaging systems that can be utilized in the intensive care unit, emergency department, and operating rooms, where moving the patient is either impracticable or ill-advised due to the risk of harm to the patient.

The image quality of the reconstruction depends upon accurate knowledge of the acquisition scan geometry, including spatial and angular positions of the x-ray source and detector for each projection. Uncertainties in the scan geometry can lead to artifacts and/or blurring in the reconstructed object. The development of portable volume imaging systems has been hampered by difficulties in accurately determining the acquisition scan geometry. There remains a need for improved X-ray volume imaging systems that can be made, or are, portable and still provide reliable clinical images and data.

Reference is hereby made to an article by S. Quadah, J. W. Stayman, G. J. Gang, A. Uneri, T. Ehtiati, and J. H. Siewerdsen entitled "Self-calibration of cone-beam CT geometry using 3D-2D image registration" in *Phys. Med. Biol.* 2016, Apr. 7; pp. 2613-2632. Reference is made to commonly assigned U.S. Pat. No. 8,821,017 (Lalena) entitled PROJECTOR AS COLLIMATOR LIGHT, which is hereby incorporated by reference herein in its entirety.

FIG. 1 is a diagram that shows a perspective view of a mobile radiography unit 100 that can be used together with portable radiographic detectors or flat panel detectors that are mechanically uncoupled from the radiation source, and the mobile radiography unit 100, according to embodiments of the application disclosed herein. The exemplary mobile x-ray or radiographic apparatus 100 of FIG. 1 can be employed for digital radiography (DR) and/or tomosynthesis or tomographic imaging. As shown in FIG. 1, a mobile radiography apparatus 100 can include a moveable transport frame 120 that includes a first display 110 and an optional second display 110' to display relevant information such as obtained images and related data, as well as operator inputs to control firing an x-ray source in x-ray tube head 140. As shown in FIG. 1, the second display 110' can be pivotably mounted at the x-ray source, x-ray tube, or x-ray head 140 to be viewable/touchable from a 360 degree area.

The displays 110, 110' can provide an input screen for an operator to implement or control (e.g., touch screens) functions such as generating, storing, transmitting, modifying, and printing of the obtained, or captured x-ray image(s), and can include an integral (e.g., touch screen) or separate control panel (not shown) to assist in implementing functions such as generating, storing, transmitting, modifying, and printing of obtained, or captured, x-ray images. An optional touchpad 150 allows support functions such as operator identification.

For mobility, the mobile radiographic apparatus 100 can have one or more wheels 115 and one or more handle grips 125, typically provided at waist-level, arm-level, or hand-level, that help an operator to move and to guide the mobile radiographic apparatus 100 to its intended location. A self-contained battery pack (e.g., rechargeable) can provide source power, which can reduce or eliminate the need for operation near a power outlet. Further, the self-contained battery pack can be configured to provide power for motorized wheels to transport the entire mobile radiography unit 100 to its intended location.

For storage, the mobile radiographic apparatus 100 can include an area/holder 135 (FIG. 2) for holding/storing one or more digital radiographic (DR) detectors 20 or computed radiography cassettes. The area/holder 135 can be a storage area disposed on the frame 120 configured to removably retain at least one digital radiography (DR) detector 20. The storage area 135 can be configured to hold a plurality of detectors 20 and can also be configured to hold one size or multiple sizes of DR detectors.

Still referring to FIG. 1, a control logic processor 130 provides the control logic for image processing and identification of the position of the detector 20 relative to the x-ray source in the tube head 140. Image processing can be provided by the control logic processor 130 that is part of mobile radiography apparatus 100 itself, or can be provided by one or more external computers, such as a control console, and other processors networked in signal communication with mobile radiography apparatus 100.

Mounted to frame 120 is a support member or column 135 that supports x-ray head 140, also called an x-ray tube, tube head, or generator, that includes the x-ray source and that can be mounted to the support member or column 135. In the embodiment shown in FIG. 1, the support member or column 135 can include a second horizontal telescoping section 30 that extends outward at a fixed or variable distance from the vertical first section where the second section is configured to ride vertically up and down the first section to the desired height for obtaining the radiographic image of a patient. In addition, the support member or column 135 vertical section is rotatably attached to the moveable frame 120 to allow manual rotation of the support member or column 135 around a vertical axis. In another embodiment, the tube head 140 can be rotatably coupled to the support column 135. In another exemplary embodiment, an articulated member of the support column that bends at a joint mechanism can allow movement of the x-ray tube head 140 over a range of vertical and horizontal positions. Height settings for the x-ray tube head 140 can range from low height for imaging feet and lower extremities to shoulder height and above for imaging the upper body portions of patients in various positions.

Figure 2:
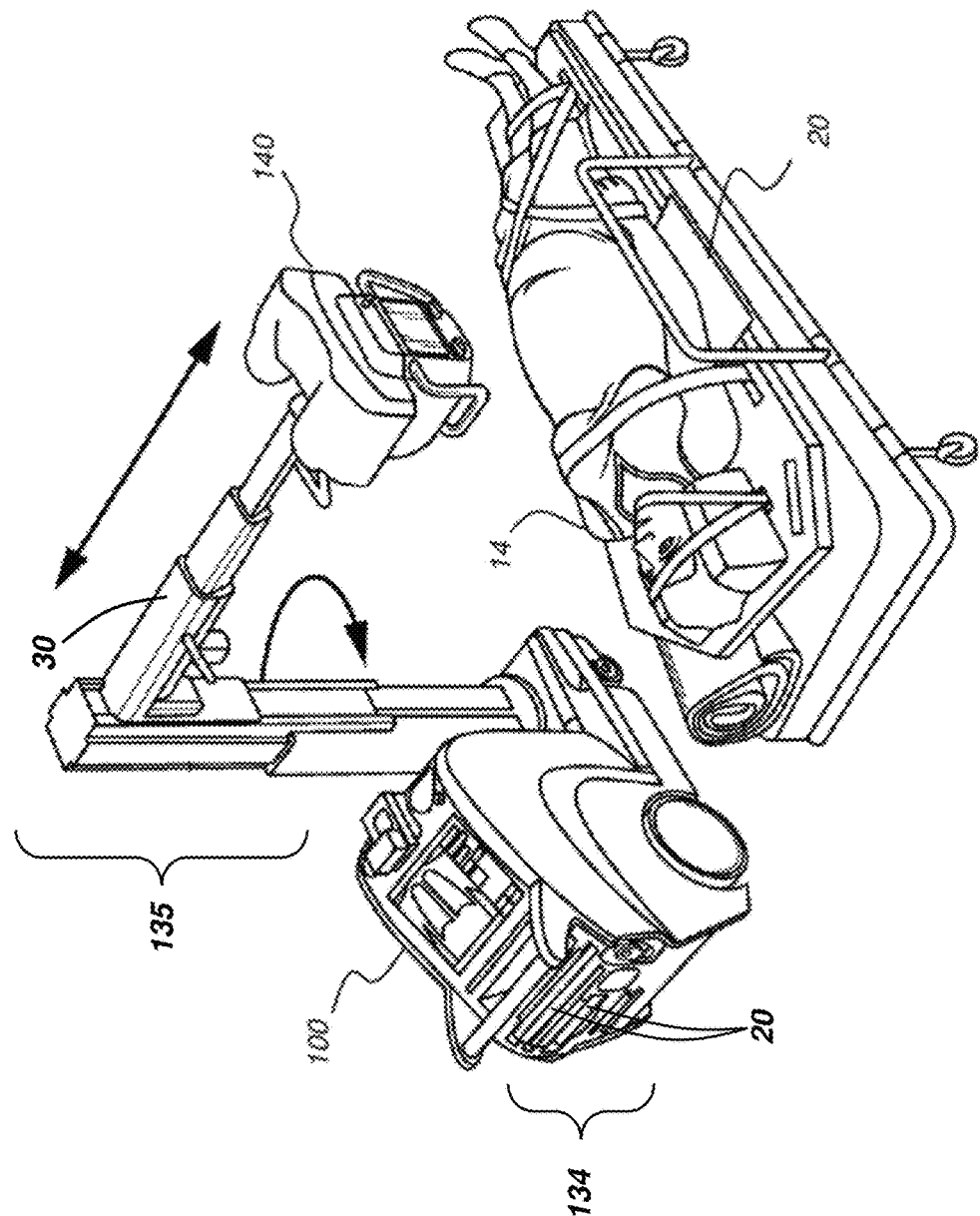
FIG. 2 is a perspective view that shows one embodiment of a mobile radiography apparatus in position for volume imaging.

The perspective view of FIG. 2 shows mobile radiography apparatus 100 in position for tomosynthesis or tomographic imaging. Telescoping horizontal section 30 of the support member or column 135 is extendible in a linear direction away from the vertical section of support member or column 135. A patient 14 is lying flat on a bed or stretcher with a detector 20 fitted behind the patient 14, with respect to the x-ray source in the tube head 140. There is no inherent mechanical linkage or alignment between x-ray tube head 140 and the detector 20, and so conventional calibration of source/detector geometry prior to exposure is not feasible.

Figure 3A:
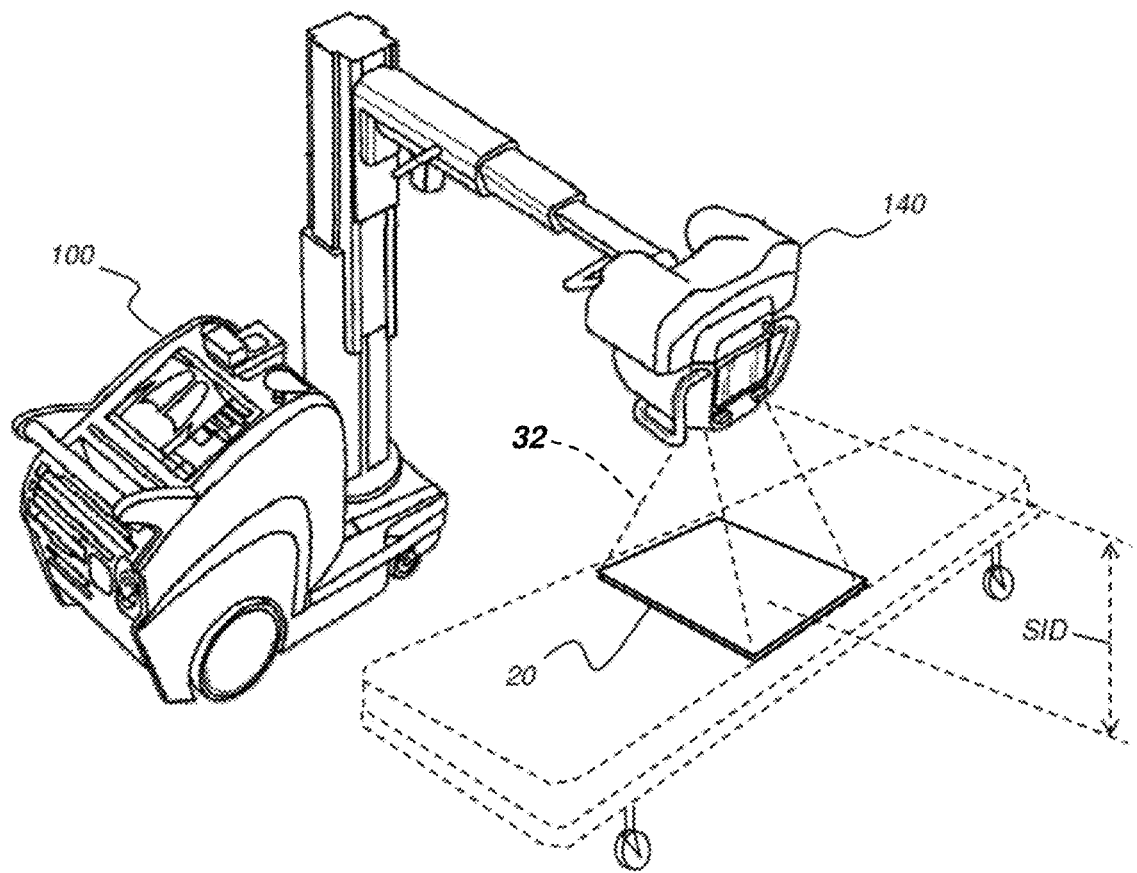
FIG. 3A is a perspective view that shows one embodiment of aspects of the image capture metrics and behavior that relate to geometric calibration for a mobile radiology apparatus when used for tomosynthesis and other volume imaging.
Figure 3B:
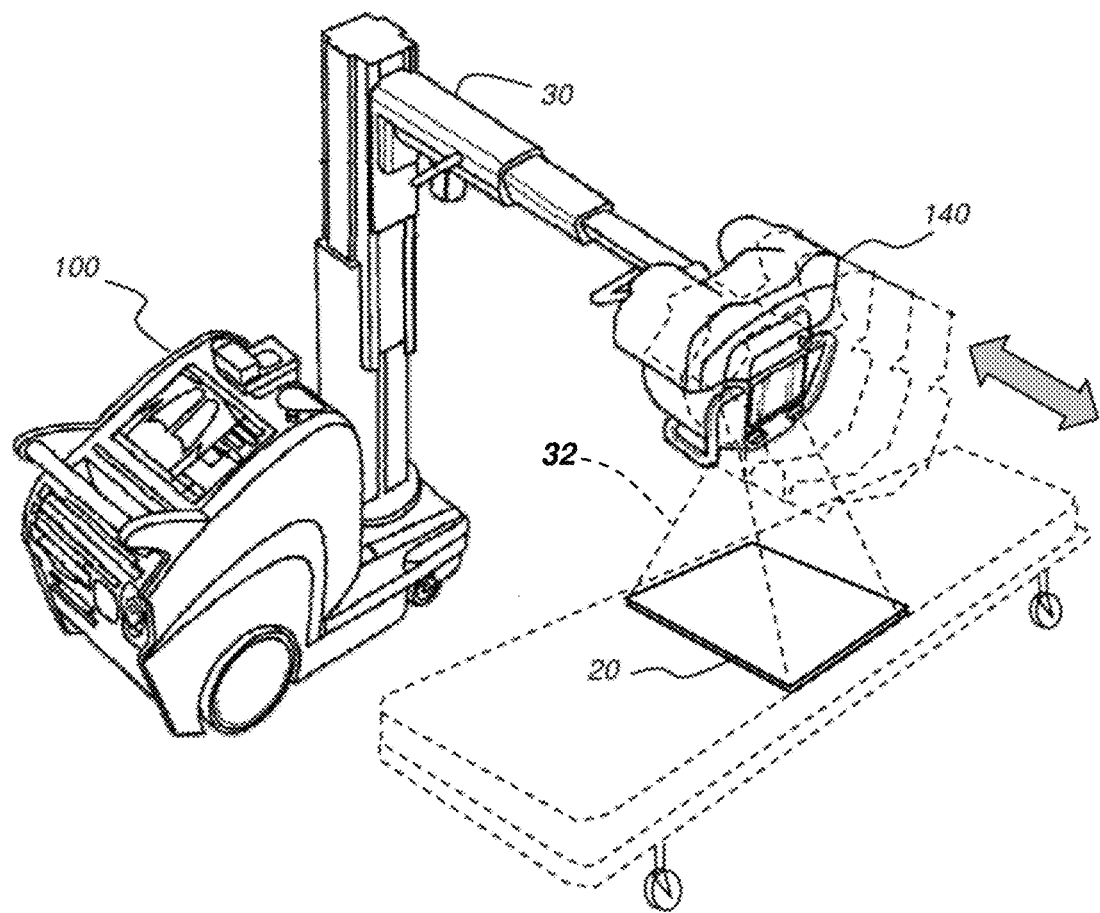
FIG. 3B is a perspective view that shows additional aspects of the image capture metrics and x-ray head translation related to geometric calibration for a mobile radiology apparatus when used for tomosynthesis and other volume imaging.

The perspective views of FIGS. 3A and 3B show aspects of the image capture metrics and behavior that relate to geometric calibration for mobile radiology apparatus 100 when used for tomosynthesis or other volume imaging. A source-to-image distance SID can be approximated based on known factors, such as bed height and column height for the mobile radiography apparatus 100. Even where the SID can be accurately identified, however, there are additional calibration metrics that must be known. These include factors such as skew of the detector 20 relative to the x-ray source in the tube head 140, as shown in FIG. 3A, and the relative travel path of the source and/or the detector as successive images are acquired. As shown in FIG. 3B, for linear travel of the tube head 140 using a telescoping transport apparatus in the horizontal portion 30 of the support member 135 may be advantageous for capturing successive projection x-ray images of a patient at different relative angles as between the x-ray source in tube head 140 and the detector 20.

Figure 4:
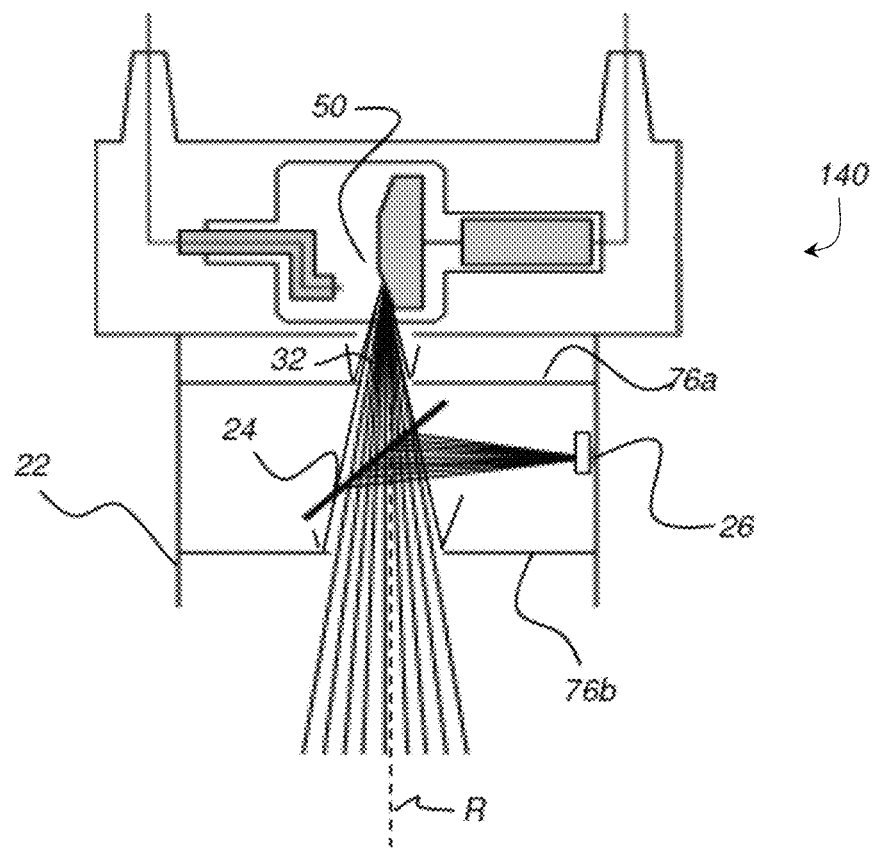
FIG. 4 is a schematic cross-section of one embodiment of a portion of a conventional x-ray tube head.

The cutaway cross-sectional schematic view of FIG. 4 shows a portion of a conventional x-ray tube head 140 having an x-ray radiation source 50 with a collimator 22 and a collimator light 26. As referred to herein, a tube head 140 may also include filters, other light sources, a plurality of x-ray sources such as cold cathode (CC) or carbon nanotube (CNT) x-ray sources, a vacuum sealed enclosure for one or more x-ray sources, a housing to enclose tube head components, a display screen which may include a touch screen, control knobs, handles for manually maneuvering the tube head into position, and other components as described herein. Collimator 22 typically has two collimator sections 76a and 76b, each with blades positioned for shaping the output radiation beam. A collimator light 26, typically a light bulb or light emitting diode (LED) or other solid-state light source, mounts inside collimator 22 and serves as a guide for aiming orientation of the x-ray head 140. A mirror 24, essentially transparent to x-rays but reflective to visible light, combines the light path of collimator light 26 with the radiation path R of x-ray beam 32 that extends from the x-ray source, so that the cross-sectional area of the light beam from collimator light 26 matches the cross-sectional area of the collimated radiation beam that is emitted from x-ray head 140.

Figure 5:
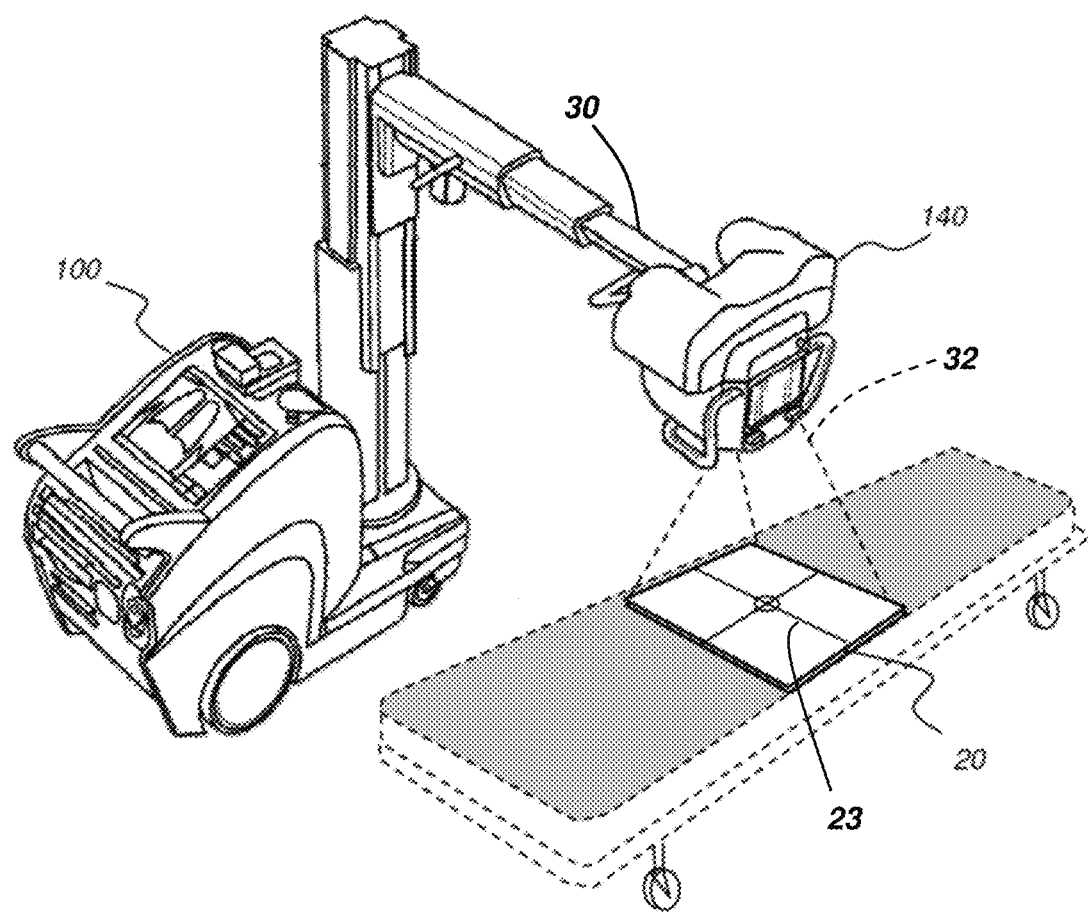
FIG. 5 is a perspective view showing the function of one embodiment of a collimator light, which projects a pattern of light to assist registration of the patient to the source.

The perspective view of FIG. 5 shows the function of collimator light 26, which typically projects a lighted pattern 23 to assist registration of the patient to the source so that the collimated beam is directed to the subject region that is properly within the perimeter of the detector 20. As has been emphasized, however, it is generally not feasible to identify the exact position and skew orientation of detector 20 relative to the x-ray beam 32 from x-ray head 140 for mobile radiography applications, for reasons such as detector placement and condition of the patient.

According to embodiments of the present disclosure, geometric calibration of the source and detector is performed using the acquired radiography image content. Radio-opaque markers 40 are disposed within or external to x-ray head 140 at fixed positions along, or proximate to, a central radiation path R in the radiation beam 32. The image content that is acquired at, or captured by, the x-ray detector 20 includes the markers 40. The position of the markers in the acquired x-ray image relates directly to the relative geometry of the x-ray source 50 and detector 20 and can be used to calculate this geometry with sufficient accuracy to provide a faithful reconstruction of depth information for the imaged patient anatomy.

Figure 6:
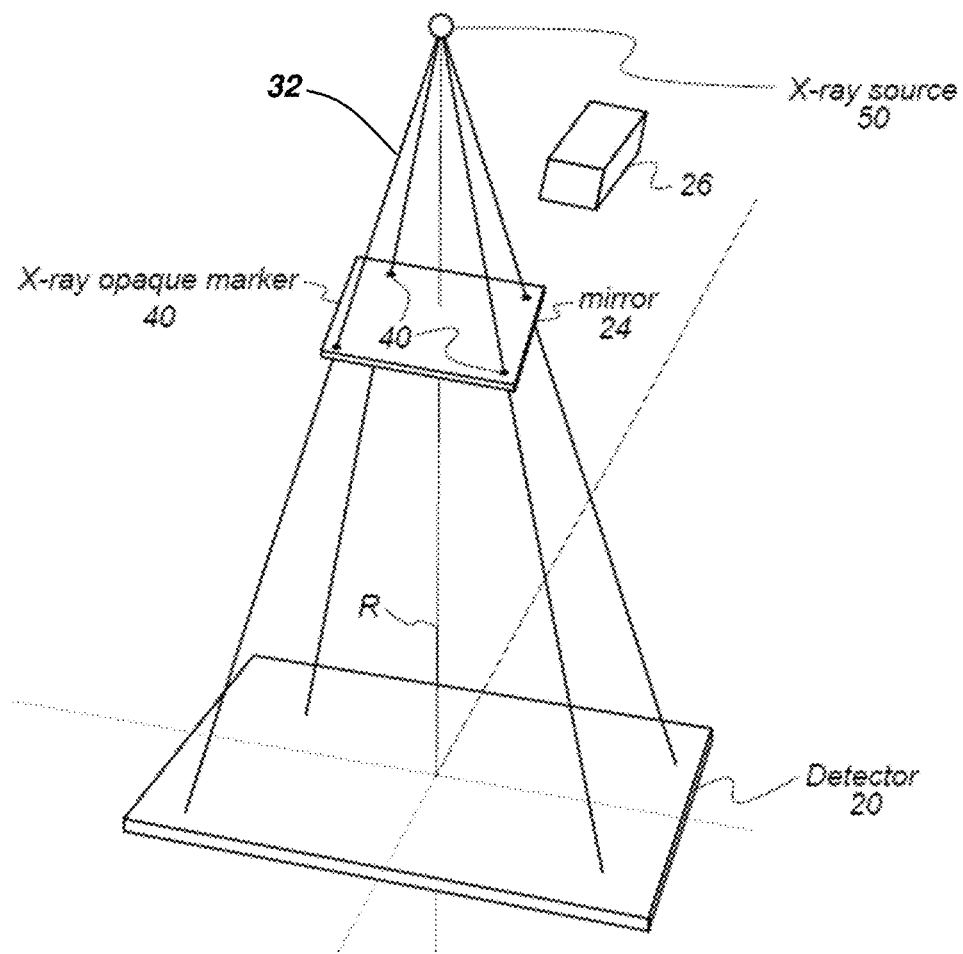
FIG. 6 is a schematic diagram showing one embodiment of components of a self-calibrating apparatus for a mobile radiography apparatus.

Referring to the simplified schematic diagram of FIG. 6, mirror 24 of x-ray head 140 is shown in relation to the position of collimator light 26 and x-ray source 50. Mirror 24 has been modified to include a set of radio-opaque markers 40, each marker 40 disposed in path R of the x-ray radiation beam 32 directed toward detector 20. Because each marker 40 is radio-opaque, the markers 40 are detected in the x-ray image content from detector 20 and so appear in the captured x-ray image visible to medical personnel so long as the marker image is not digitally removed or erased. The pattern of markers 40 that are imaged by detector 20 and the overall geometry of the detected pattern provide sufficient information for an accurate spatial calibration of detector 20 relative to a position of x-ray source 50.

It should be noted that, while mirror 24 can be a convenient vehicle for mounting of the radio-opaque markers within x-ray head 140, other components within the x-ray head 140 that lie in the radiation path R can alternately be used, such as filters, for example. The markers can be coupled to, or formed as part of, a suitable radio transparent, or radiolucent, support surface or to some other feature that is in the path of the radiation beam and collimator light. In one embodiment, a radiolucent marker substrate, or support surface, having radiopaque markers therein, may be inserted into, or otherwise attached to, the tube head.

There are a number of considerations that relate to marker use for geometric calibration of a mobile radiography apparatus, including the following:

(i) Marker positioning along the periphery of the radiation field. Peripheral positions of markers 40 with respect to the detector imaging area are generally advantageous. Anatomical information of interest is generally centered in the image area; markers 40 along the edges or outside of the imaged area are less likely to interfere with 3D reconstruction.

(ii) Fixed positioning. Marker positions may be fixed inside or outside the housing of the x-ray head 140 and their locations do not change relative to the x-ray source or sources with adjustment of tube head 140 position. If markers 40 are provided on the mirror 24 as disclosed with reference to FIG. 4, the mirror 24 should be in a fixed position within the tube head 140.

(iii) Calibration of markers 40 to head 140. An initial geometric calibration of markers 40 position to the head 140 and x-ray source 50 is performed as a setup procedure for the mobile radiography apparatus, prior to use of markers 40 for source/detector calibration for a patient image. This calibration may include separation distance between markers 40 on the marker substrate, whether the substrate is the mirror 24 or a separate substrate.

(iv) Shadows. Markers 40 generate shadows in the acquired projection images, i.e., marker images appear in the acquired x-ray images. Additional image processing steps are needed in order to remove the marker images, or shadows, following geometric calibration. Well-known image processing procedures such as segmentation, interpolation, and in-painting can be employed to compensate for shadow effects.

(v) High magnification factor. The geometry magnification factor for markers is significant. Thus, the markers 40 themselves should be made as small and distinct as possible.

(vi) Marker shape. Specially shaped markers 40 facilitate marker detection and removal from the projection images. For example, circular, triangular, or cross-shaped markers 40 may be advantaged. Although the marker shape may increase marker size, distinctive shapes can help to simplify detection of the center of the marker, allowing ready identification and removal.

(vii) Adjustable collimators. Depending on the design of x-ray head 140, collimators 22 may be adjustable. This factor must be taken into account for marker design and positioning. A specific collimator position may work best for subsequent detection and removal of marker effects.

Calibration of marker position (item (iii) above) can be performed by establishing precise positional coordinates for detector 20 relative to x-ray source 50 and acquiring image content from two or more exposures along the travel path of x-ray head 140. Calibration of marker position can then be calculated from positional and movement information from the resulting sequence of projection images, using well known methods of triangulation and projective geometry.

Using the initially calibrated marker 40 position with respect to x-ray source 50, metrics such as SID, skew, and planar orientation of the detector 20 can be readily computed using well-known projective geometry calculations.

Figure 7:
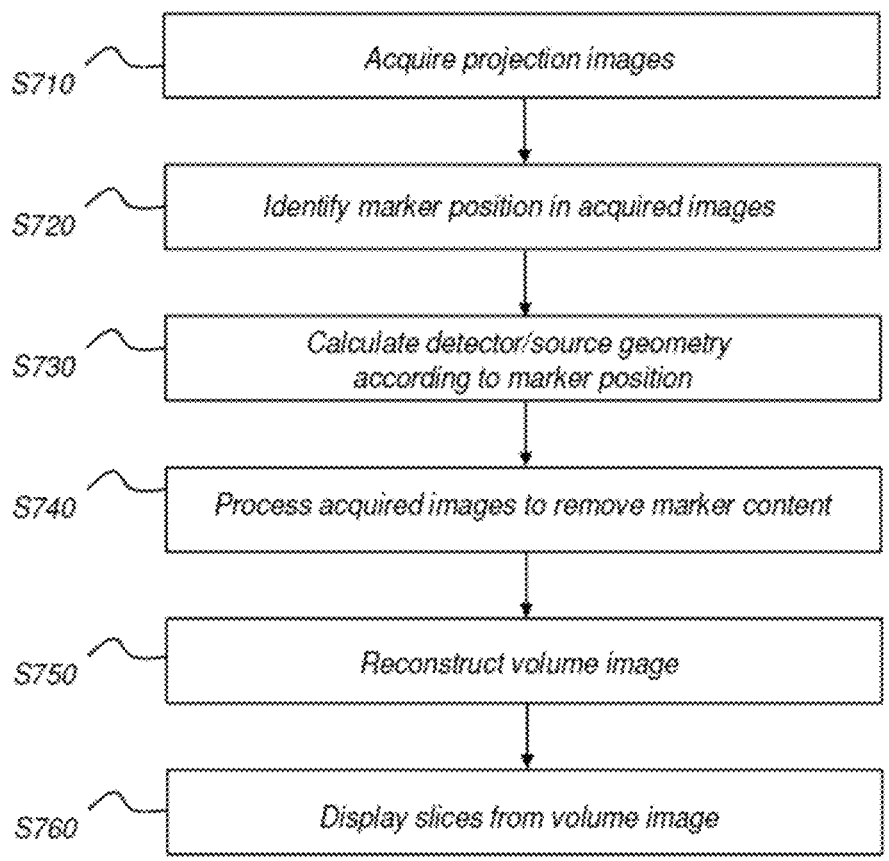
FIG. 7 is a logic flow diagram that shows one embodiment of a sequence for calibration of a mobile radiography apparatus having a detector that is not mechanically coupled to the x-ray source.

The logic flow diagram of FIG. 7 shows a sequence for calibration of a mobile radiography apparatus having a detector that is not mechanically coupled to the x-ray source and wherein (i) the apparatus is configured with markers and (ii) marker calibration to the x-ray source has been performed. A set of 2D projection images of the subject is acquired for processing in an image acquisition step S710. Marker positions in the projection images are then identified in an identification step S720. A calculation step S730 then calculates detector/source geometry based on identified marker position, using well known projective geometry processing. A cleanup step S740 is then executed, in which marker content is removed from the projection images. Cleanup step S740 can use interpolation, in-painting, and other well known processes in order to restore image content and remove marker shadows, as noted previously. This can be readily accomplished, since the markers have the same position in each acquired projection image. A reconstruction step S750 can then be executed in order to generate the 3D volume image from corrected 2D projection images. Reconstruction methods for tomography and tomosynthesis imaging are well known and include filtered back projection (FBP) and iterative reconstruction methods, allowing a number of processing sequences to be used for volume image reconstruction. 2D slices or other portions or projections of the generated 3D volume image can then be extracted and displayed in a display step S760.

According to an embodiment of the present disclosure, only a portion of the acquired projection images in a tomosynthesis series or tomography series are analyzed for marker position detection and calculation of source/detector geometry in step S730.

Using radio-opaque markers embedded along the radiation path and executing the process outlined with respect to FIG. 7, an embodiment of the present disclosure enables source/detector geometry to be calculated from the set of projection images that is acquired. Thus, embodiments of the present disclosure are advantageous for calibration use with mobile radiography apparatus and other radiography systems in which the imaging detector is mechanically uncoupled from the radiation source.

As described herein, markers 40 can be formed of lead or other radio-opaque material, including metals such as tungsten. Markers can be formed into three dimensional volumetric beads, cubes, or into some other dimensionally suitable shape, such as a substantially flat cross or circle, a square, a triangle, or some other shape and can be adhered, imprinted by deposition onto, or embedded into, a radio-transparent, or radiolucent, surface, or otherwise coupled to a mirror, filter, or other permanent feature of, such as being attached to, the x-ray tube head 140. Markers 40 can be coupled to a radio-transparent support feature, such as onto a planar glass or plastic surface or feature, that is in the path of collimated x-ray energy from one or more x-ray sources in the tube head 140.

The following references are cited:

Yuan Lin and Ehsan Samei, "A FAST POLY-ENERGETIC FBP ALGORITHM", Physics in Medicine and Biology 59 (2014) pp. 1655-1678;

Yuan Lin and Ehsan Samei, "AN EFFICIENT POLYENERGETIC SART (pSART) RECONSTRUCTION ALGORITHM FOR QUANTITIVE MYOCARDIAL CT PERFUSION", Medical Physics, 41 (2) February 2014, pp. 021911-1 to 021911-14;

F. Edward Boas and Dominik Fleischmann, "CT ARTIFACTS: CAUSES AND REDUCTION TECHNIQUES", Imaging Med. (2012) 4 (2), 229-240;

US 2008/0095302 (Ruhrnschopf) titled "METHOD FOR HARDENING CORRECTION IN MEDICAL IMAGING";

WO 2016/003957 (Lin) titled "SPECTRAL ESTIMATION AND POLY-ENERGETIC RECONSTRUCTION METHODS AND X-RAY SYSTEMS" published on Jan. 7, 2016.

Figure 8C:
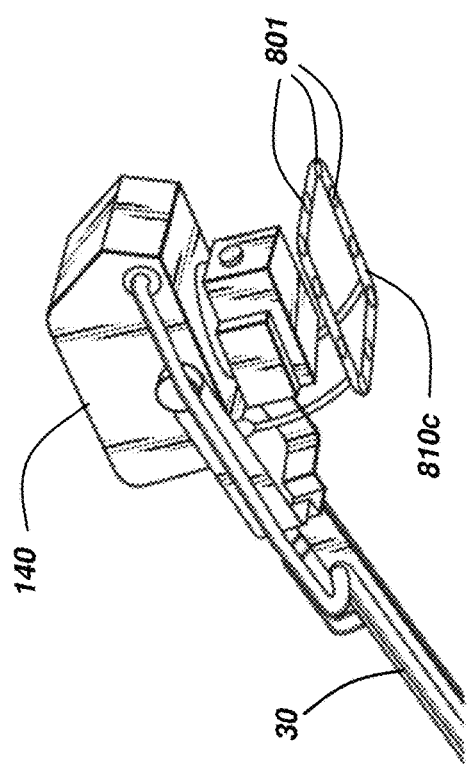
Figure 8D:
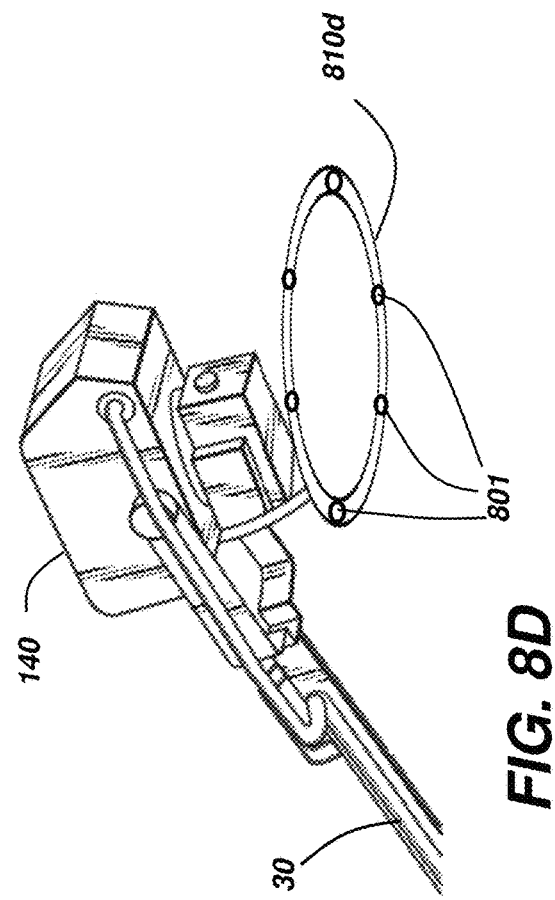
Figure 8E:
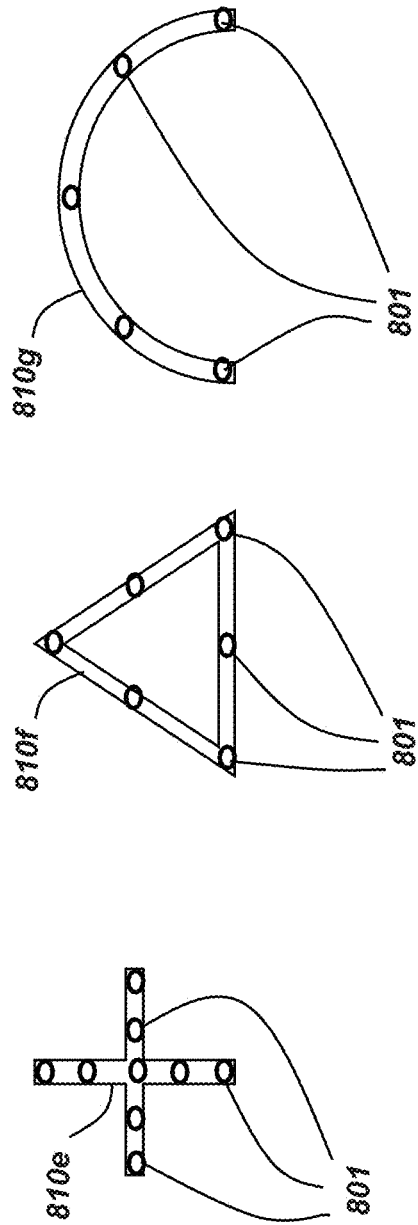

Turning to FIGS. 8A-8D, a tube head 140 may include multiple x-ray sources in the form of cold cathode or CNT x-ray sources 801 attached to a source support member 810a-d. In one embodiment, six x-ray sources 801 may be arranged linearly using a linear source support member 810a. In one embodiment, seven x-ray sources 801 may be arranged angularly using an angular source support member 810b. In one embodiment, ten x-ray sources 801 may be arranged rectilinearly using a rectangular source support member 810c. In one embodiment, six x-ray sources 801 may be arranged circularly using a circular source support member 810d. X-ray source arrangements having a plurality of x-ray sources may be configured to controllably fire one or more of the x-ray sources once or in a programmed sequence, such as for acquiring a number of projection x-ray images to be used in a volume x-ray image reconstruction. In one embodiment, multiple cold cathode or CNT sources 801 supported by linear support member 801a may be programmably fired in a timed sequence to capture a series of x-ray projection images quickly, without requiring movement of a single-source tube head along a linear path such as shown in the embodiment of FIG. 3B. FIG. 8E shows additional exemplary patterns or arrangements of x-ray sources 801 secured to source support members 810e, 810f, and 810g, in a cross shape, a triangular shape, and a curvilinear shape, respectively, which are operatively attachable to, and usable with, tube head 140 similar to the embodiments of FIGS. 8A-8D. The arrangement of x-ray sources or number of x-ray sources per arrangement are not limited to the examples disclosed herein and may vary to any extent desired.

Figure 9:
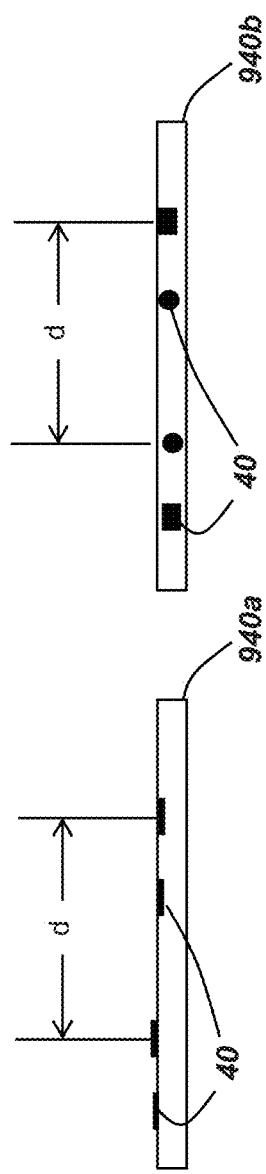
FIG. 9 illustrates different configurations of markers.

FIG. 9 is a schematic diagram of side views of exemplary radiolucent planar marker substrates 940a, 940b, having radiopaque markers 40 supported thereby, as described herein. The marker substrates 940a, 940b, may be made from glass, plastic or other suitable radiolucent material. As disclosed herein, radiopaque markers 40 may be shaped as substantially flat circular, triangular, square, cross, or other shape markers 40, deposited onto a surface of, embedded at any desired depth into a surface of, or otherwise supported by, marker substrate 940a. Similarly, radiopaque markers 40 may be shaped as volumetric spheres, cubes, or other three dimensional shape markers 40, embedded into the radiolucent substrate or otherwise supported by marker substrate 940b. In one embodiment, distances d between selected ones of the radiopaque markers 40 are precisely known. In one embodiment, distances d between all markers 40 supported by marker substrate 940a, 940b, are precisely known.

Figure 10:
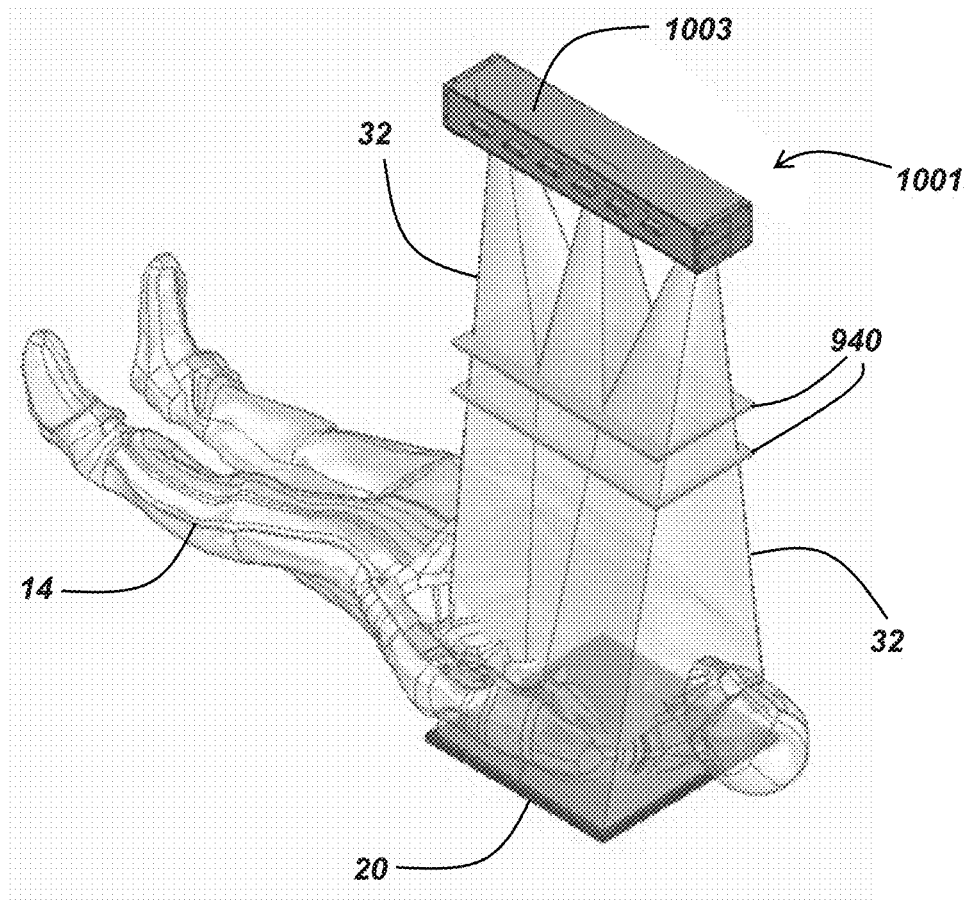
FIG. 10 is a schematic showing a one embodiment of a multiple source tube head and multiple radiopaque marker surfaces positioned in x-ray beams.

FIG. 10 is a schematic diagram of an exemplary imaging system including a tube head 1001 having a housing 1003 enclosing a plurality of CC or CNT x-ray sources each configured to emit an x-ray beam 32, when activated, toward DR detector 20 to capture x-ray projection images of a portion of a patient 14. In the exemplary embodiment of FIG. 10, two radiolucent marker substrates 940 are used simultaneously, each having a plurality of radiopaque markers supported thereby (markers not shown) in the x-ray beams 32 emitted by the x-ray sources. Each of the marker substrates 940 is positioned at a different distance from the tube head 1001.

Figure 11:
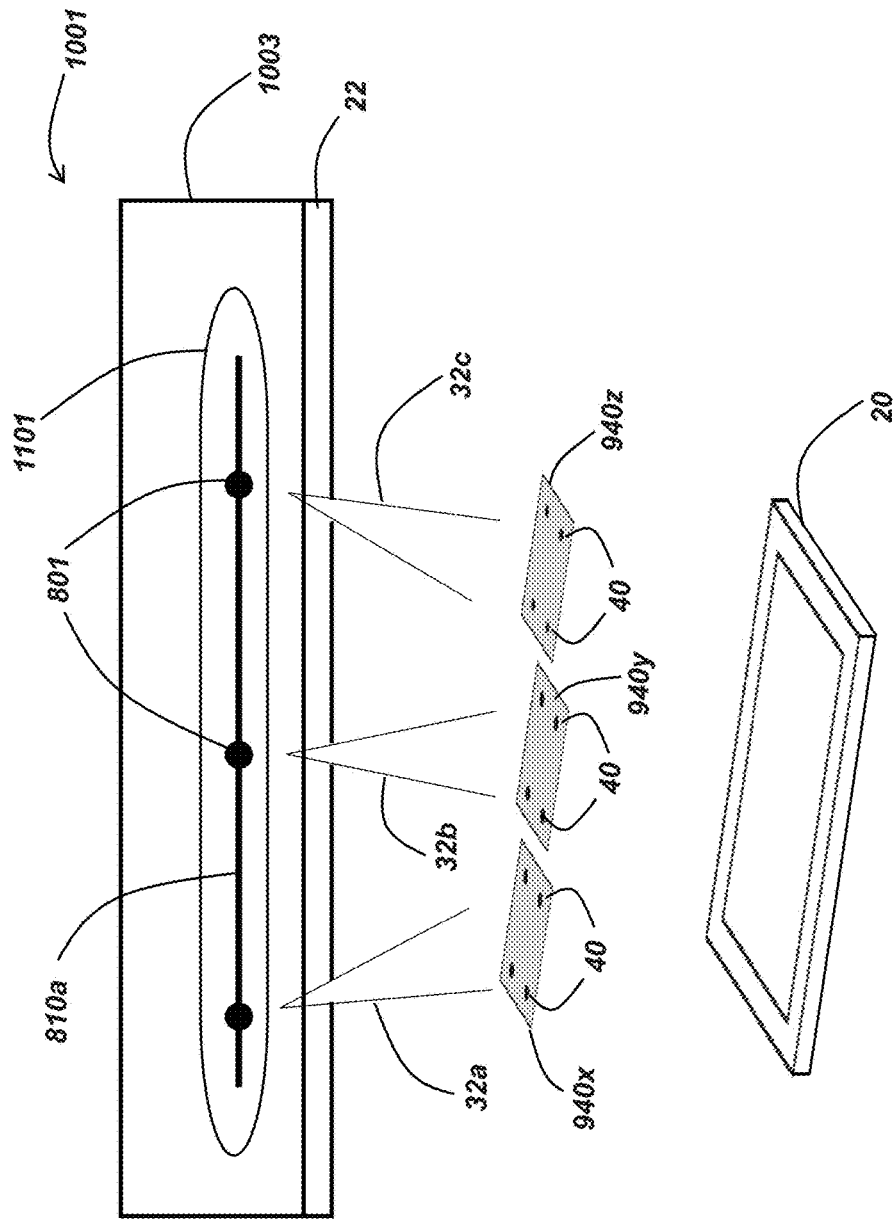
FIG. 11 is a schematic of one embodiment of a tube head and marker positioning.

FIG. 11 is a schematic diagram of a tube head housing 1003 enclosing a plurality of CC or CNT x-ray sources 801 each configured to emit an x-ray beam 32a, 32b, 32c, toward DR detector 20. Collimator section 22 of tube head 1001 selectively collimates the x-ray beams 32a-32c. The x-ray sources 801 may each be enclosed in a different vacuum chamber, or vacuum tube, or, as shown in FIG. 11, the x-ray sources 801 may all be enclosed by, or sealed in, a single vacuum chamber 1101. The x-ray sources 801 are each configured to emit, when activated, an x-ray beam 32a, 32b, 32c, that travels through one corresponding radiolucent marker substrate 940x, 940y, 940z, respectively, that supports and disposes a plurality of radiopaque markers 40 within each of the corresponding x-ray beams 32a, 32b, 32c, which radiopaque markers 40 are captured in projection x-ray images acquired by DR detector 20. In the exemplary embodiment of FIG. 11, the markers 40 and their corresponding marker substrates 940x, 940y, 940z, are secured in positions within corresponding x-ray beams 32a, 32b, 32c, outside of the tube head housing 1003. In the exemplary embodiment of FIG. 11, the x-ray sources 801 are fired one at a time in a programmed sequence, thereby emitting x-ray beams 32a, 32b, 32c, one at a time, while the DR detector 20 captures one projection x-ray image for each firing of an x-ray source. In the exemplary embodiment of FIG. 11, the x-ray sources 801 are shown to be arranged linearly along linear source support member 810a, however, a suitable tube head housing 1003 may be used to enclose any shape arrangement of x-ray sources 801 disclosed herein, such as in FIGS. 8B-8E.

Figure 12:
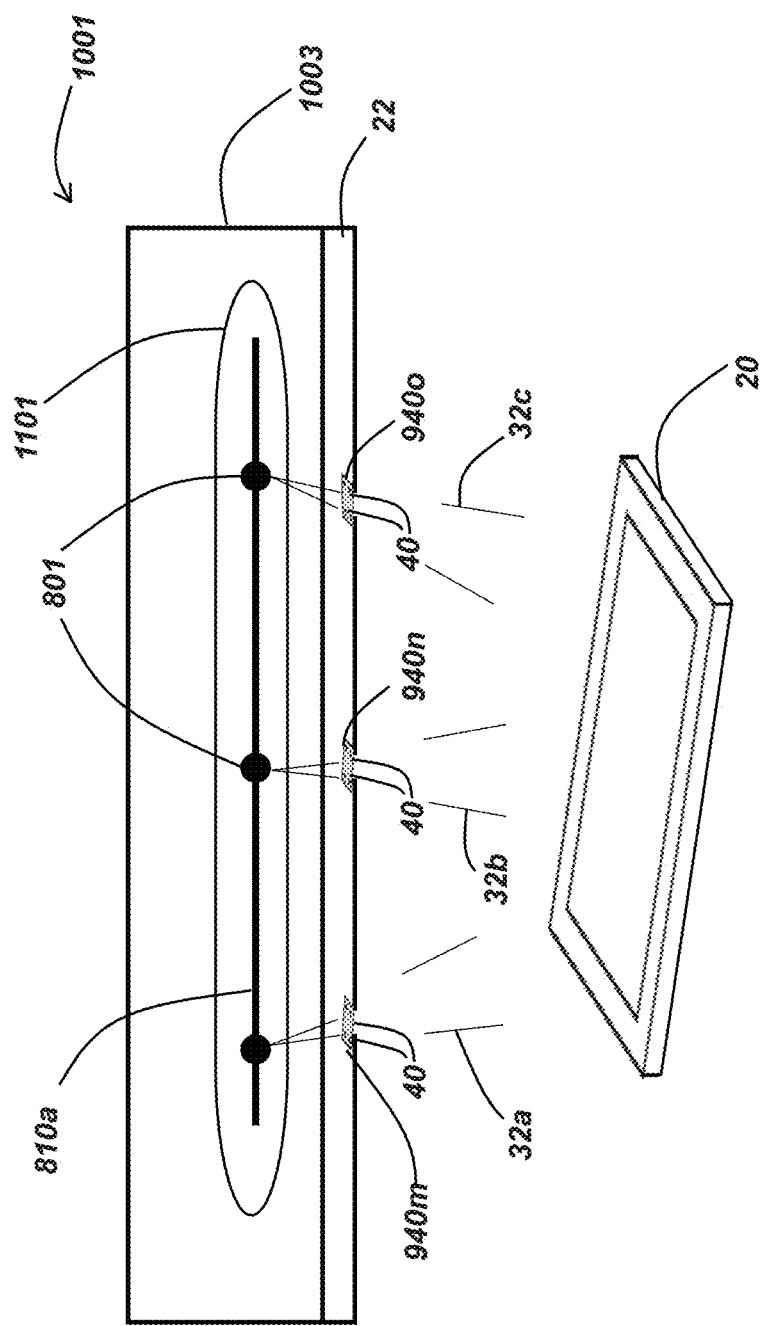
FIG. 12 is a schematic of another embodiment of a tube head and marker positioning.

FIG. 12 is a schematic diagram of a tube head housing 1003 enclosing a plurality of CC or CNT x-ray sources 801 each configured to emit an x-ray beam 32a, 32b, 32c, toward DR detector 20. The x-ray sources 801 may each be enclosed in a different vacuum chamber, or vacuum tube, or, as shown in FIG. 12, the x-ray sources 801 may all be enclosed by, or sealed in, a single vacuum chamber 1101. The x-ray sources 801 are each configured to emit, when activated, an x-ray beam 32a, 32b, 32c, that travels through one corresponding radiolucent marker substrate 940m, 940n, 940o, respectively, that supports a plurality of radiopaque markers 40 therein within each of the corresponding x-ray beams 32a, 32b, 32c, which markers 40 are captured in projection x-ray images acquired by DR detector 20. In the exemplary embodiment of FIG. 12, the markers 40 and their corresponding marker substrates 940m, 940n, 940o, are secured in positions within corresponding x-ray beams 32a, 32b, 32c, inside of the tube head housing 1003. Because the marker substrates 940m, 940n, 940o, are positioned closer to the x-ray sources 801 in the embodiment of FIG. 12, the marker substrates 940m, 940n, 940o, are sized smaller than the marker substrates 940x, 940y, 940z, in the embodiment of FIG. 11. The marker substrates 940m, 940n, 940o, may be attached to interior portions of tube head housing 1003. In the exemplary embodiment of FIG. 12, similar to the embodiment of FIG. 11, the x-ray sources 801 are fired one at a time in a programmed sequence, thereby emitting x-ray beams 32a, 32b, 32c, one at a time, while the DR detector 20 captures one projection x-ray image for each firing of an x-ray source 801. In the example embodiment of FIG. 12, the x-ray sources 801 are shown to be arranged linearly along linear source support member 810a, however, a suitable tube head housing 1003 may be used to enclose any shape arrangement of x-ray sources 801 disclosed herein.

Figure 13:
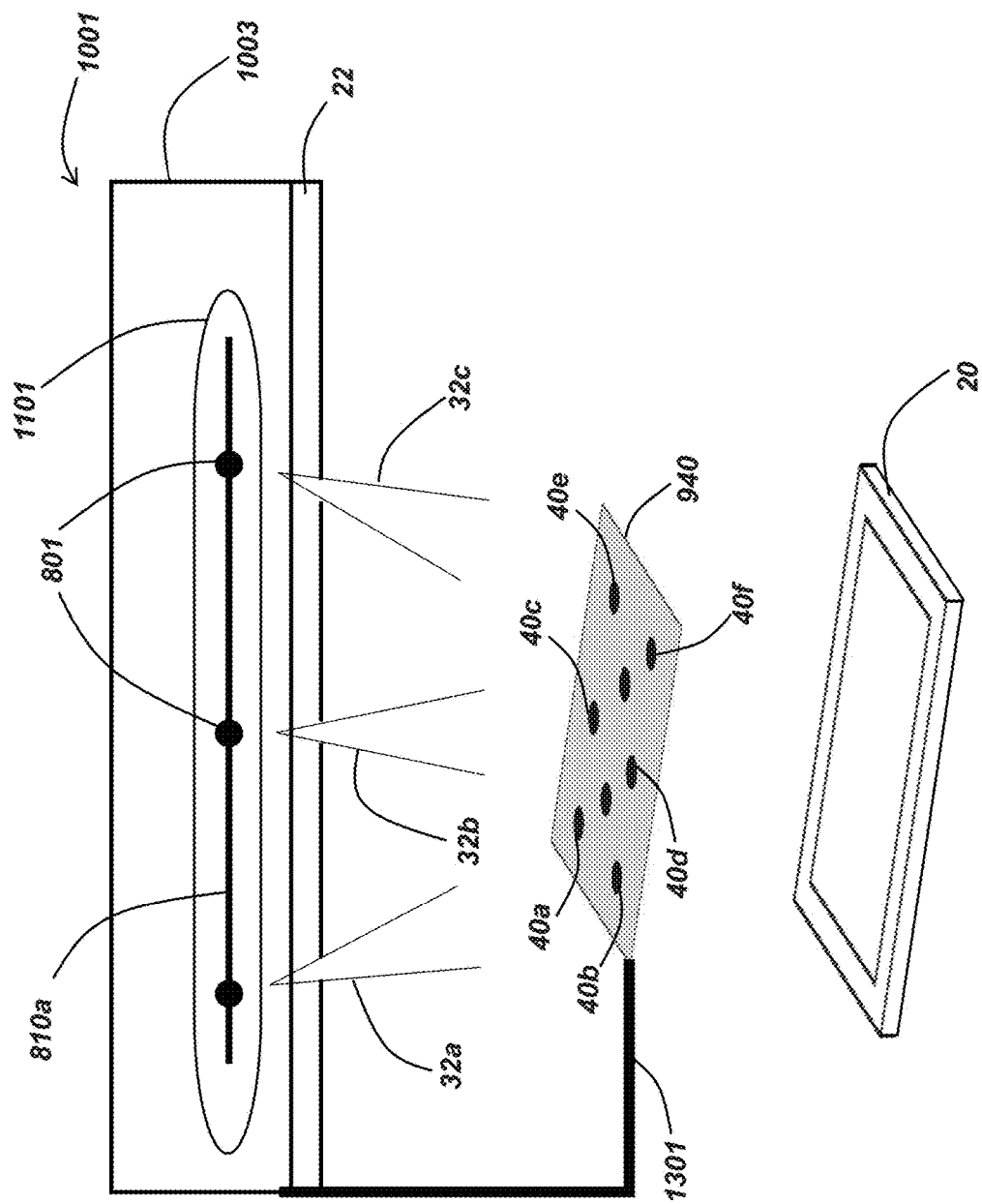
FIG. 13 is a schematic of another embodiment of a tube head and marker positioning.

FIG. 13 is a schematic diagram of a tube head housing 1003 enclosing a plurality of CC or CNT x-ray sources 801 each configured to emit an x-ray beam 32a, 32b, 32c, toward DR detector 20. The x-ray sources 801 may each be enclosed in a different vacuum chamber, or vacuum tube, or, as shown in FIG. 13, the x-ray sources 801 may all be enclosed by, or sealed in, a single vacuum chamber 1101. The x-ray sources 801 are each configured to emit, when activated, an x-ray beam 32a, 32b, 32c, that travels through a radiolucent marker substrate 940 that supports a plurality of radiopaque markers 40a-40f. At least a subset of the radiopaque markers 40a-40f are positioned in each of the x-ray beams 32a, 32b, 32c, which markers 40a-40f that are in an x-ray beam 32a, 32b, 32c, during imaging are captured in projection x-ray images acquired by DR detector 20. In a preferred embodiment, at least three of radiopaque markers 40a-40f are disposed in an activated x-ray beam 32a, 32b, 32c, during image capture, and appear in each radiographic image acquired by DR detector 20. In one exemplary embodiment, markers 40a, 40b, and at least one other marker may be positioned within x-ray beam path 32a during image capture. In another exemplary embodiment, markers 40c, 40d, and at least one other marker may be positioned within x-ray beam path 32b during image capture. In another exemplary embodiment, markers 40e, 40f, and at least one other marker may be positioned within x-ray beam path 32c during image capture. In another exemplary embodiment, markers 40a-40f may all be positioned within each of x-ray beam paths 32a-32c to be captured in corresponding images acquired by DR detector 20. In the exemplary embodiment of FIG. 13, similar to the embodiment of FIG. 11, the x-ray sources 801 are fired one at a time in a programmed sequence, thereby emitting x-ray beams 32a, 32b, 32c, one at a time, while the DR detector 20 captures one projection x-ray image for each firing of an x-ray source 801 which captured projection images each include at least three of the radiopaque markers supported by substrate 940 appearing therein.

In the exemplary embodiment of FIG. 13, the marker substrate 940 is secured in position within the x-ray beams 32a, 32b, 32c, using a rigid support arm 1301 attached to a portion of tube head 1001, or support arm 1301 may be attached to another portion of mobile radiography apparatus 100, or it may be independently supported. In the example embodiment of FIG. 13, the x-ray sources 801 are shown to be arranged linearly along linear source support member 810a, however, tube head housing 1003 may be used to enclose any shape arrangement of x-ray sources 801 disclosed herein.

Figure 14:
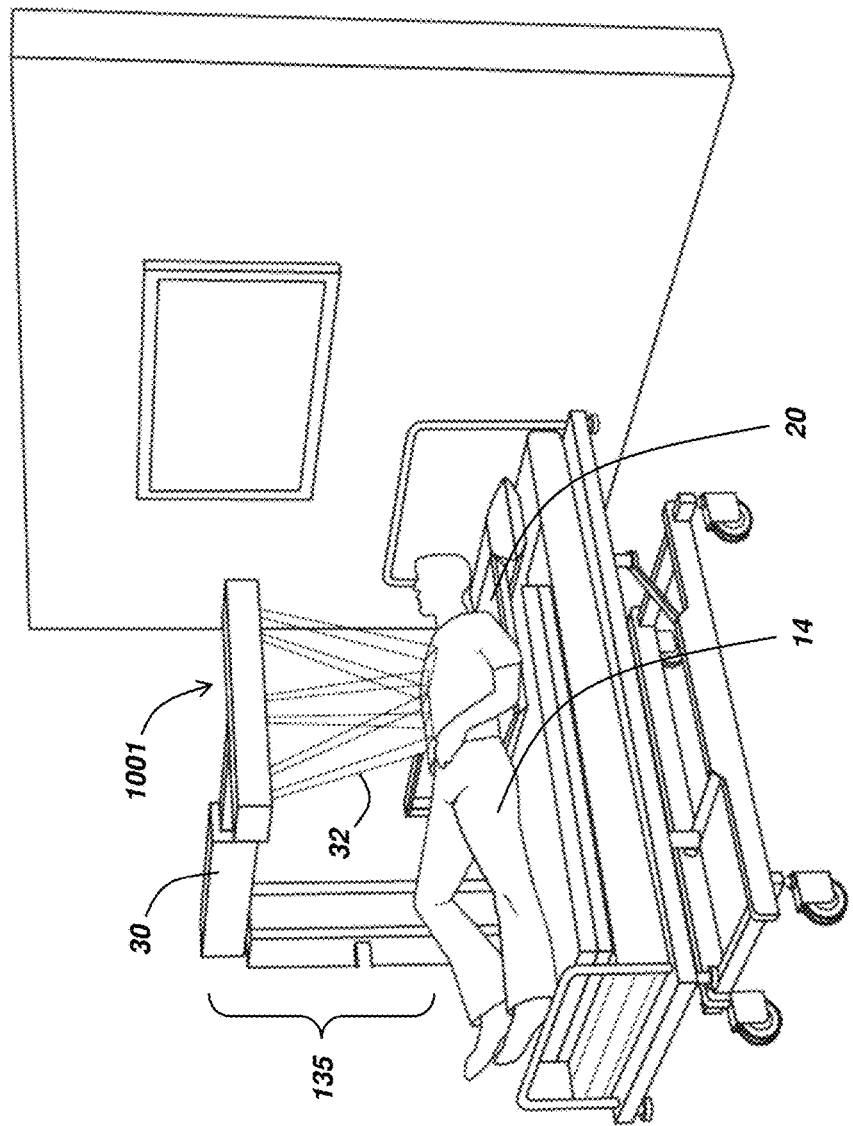
FIG. 14 illustrates patient positioning and one embodiment of a multiple source tube head.
Figure 15:
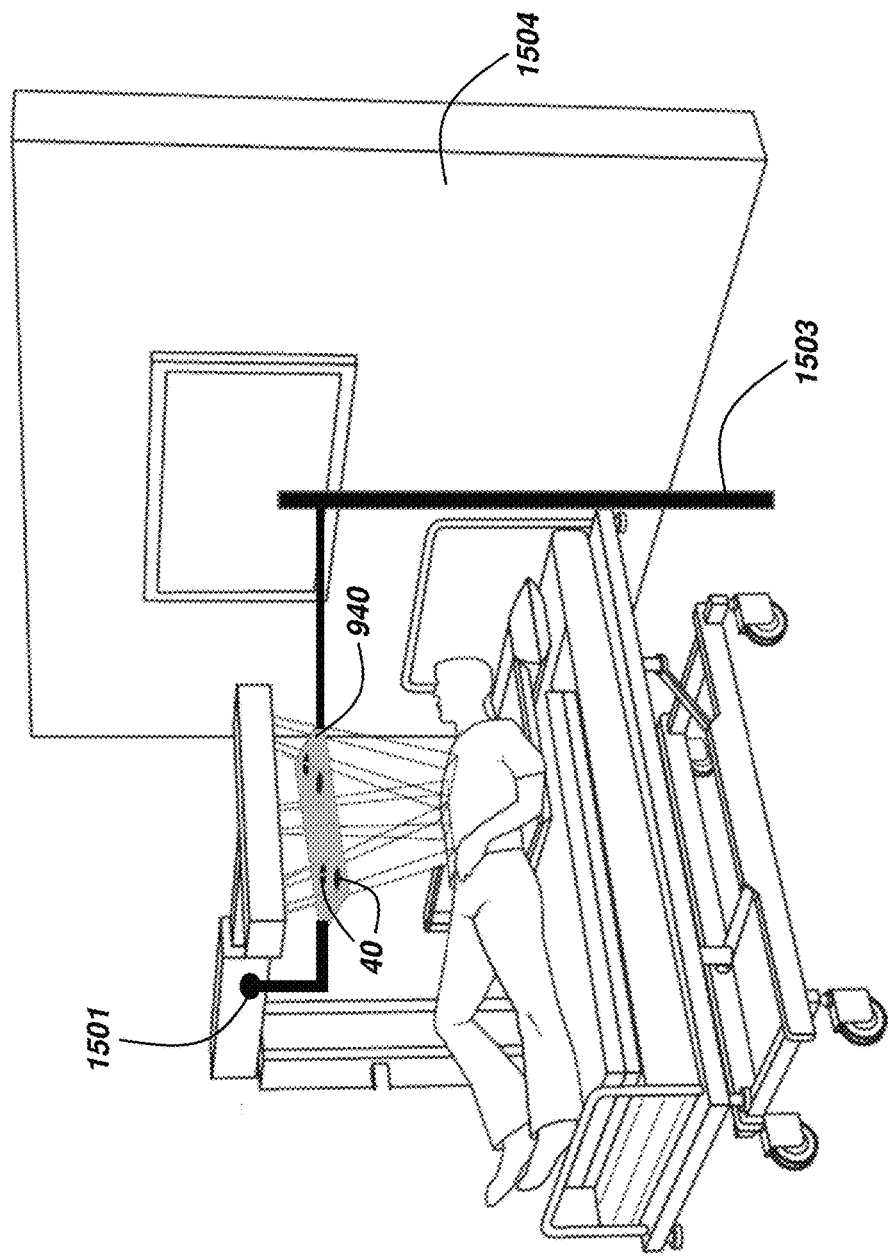
FIG. 15 illustrates patient positioning and one embodiment of a multiple source tube head and alternative mounts for radiopaque markers.

FIG. 14 is a perspective view of a mobile radiography apparatus 100 guided into position at the bedside of a patient 14 in a medical imaging facility. The horizontal section 30 of support member 135 includes tube head 1001, as described herein, attached thereto. In the embodiment of FIG. 14, x-ray sources within the tube head 1001 are configured to emit at least three x-ray beams 32, as described herein, toward DR detector 20 to capture projection images of a portion of the patient 14, as described herein. FIG. 15 illustrates the arrangement of FIG. 14 having rigid support arm 1501 attached to the horizontal section 30 of support member 135 (FIG. 14) and to the radiolucent marker substrate 940 to secure in position the radiopaque markers 40, supported by marker substrate 940, in the path of x-ray beams 32 (FIG. 14), as described herein with respect to FIG. 13. In one embodiment, support arm 1501 may be attached to radiolucent marker substrate 940 and to another portion of the mobile radiography apparatus 100, such as to the vertical section of the support member 135 (FIG. 14). In one embodiment, the radiolucent marker substrate 940 may be attached to a rigid support arm 1503 that is independently fixed in position, without attachment to any portion of the mobile radiography apparatus, such as by attachment to a floor of an x-ray imaging facility as shown in FIG. 15, or to another structural portion of an x-ray imaging facility, such as a ceiling or a wall 1504 of the imaging facility.

Figure 16:
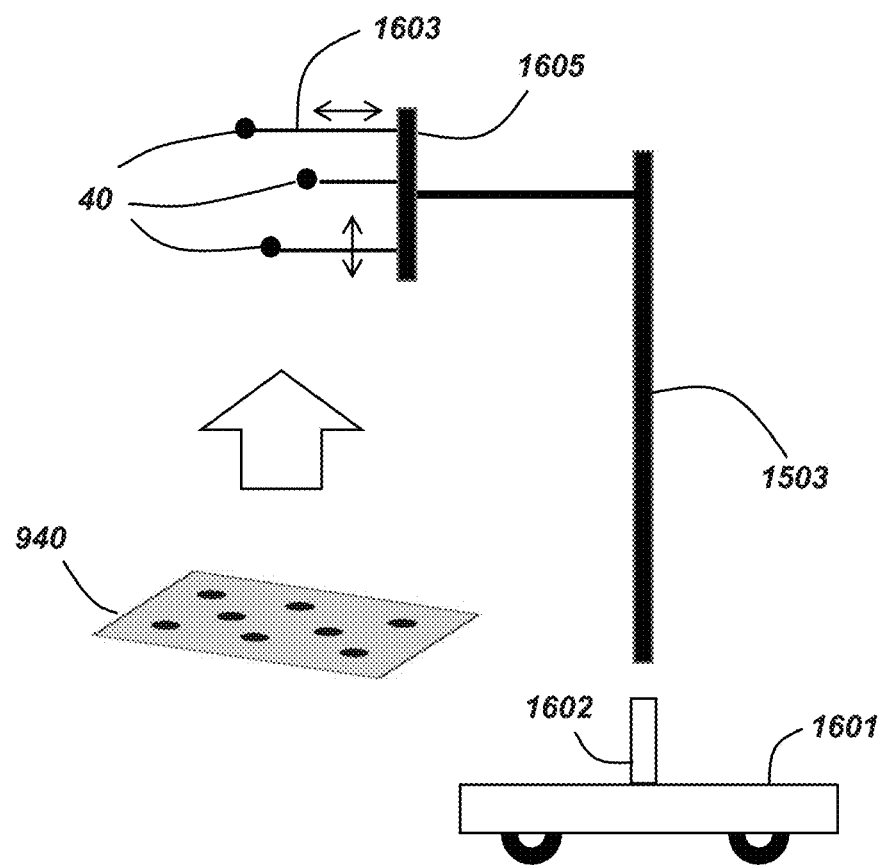
FIG. 16 is a schematic of one embodiment of a marker support holder.

With reference to FIG. 16, rigid support arm 1503 may have marker substrate 940 attached thereto, as shown in FIG. 15, or a different marker support structure attached thereto. Rigid support arm 1503 may be rigidly attached to a wheeled transport frame 1601 by sliding rigid support arm 1503 into a hollow support pillar 1602. The transport frame 1601 together with rigid support arm 1503 secured thereto, and either marker substrate 940 or a different marker support structure attached to rigid support arm 1503, may be manually guided into place at a patient bedside for positioning radiopaque markers 40 in the path of x-ray beams for radiographic imaging as described herein. In one embodiment, radiopaque markers 40 may each be individually attached to radiolucent support rods 1603 which, in turn, are movably attached to a support frame 1605, which support frame 1605 is rigidly attached to the rigid support arm 1503. The support frame 1605 may also be made from a radiolucent material. Each of the radiolucent support rods 1603 may be movable horizontally and vertically, as shown by the arrows in FIG. 16, to manually space apart the radiopaque markers 40, as desired. In addition, the assembly of radiopaque markers 40, radiolucent support rods 1603, and support frame 1605, may be detached from rigid support arm 1503 in order to swap in the marker substrate 940. Thus, the assembly of radiopaque markers 40, radiolucent support rods 1603, and support frame 1605, may be attached to rigid support arm 1503 in place of marker substrate 940, and also be guided into position, at a patient bedside as shown in FIG. 15, to place the radiopaque markers 40 in the path of x-ray beams for radiographic imaging as described herein. Although three radiopaque markers 40 are shown attached to three radiolucent support rods 1603, the support frame 1605 may include more than three support rods 1603 each having a radiopaque marker 40 attached thereto.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A mobile radiography system comprising:
a plurality of x-ray sources;
a radiographic detector mechanically uncoupled from the x-ray sources;
a plurality of radiopaque markers, the radiopaque markers disposed in one or more radiation paths each extending from one of the x-ray sources to the radiographic detector; and
a processor programmed to calculate a position of the radiographic detector relative to one or more of the plurality of x-ray sources according to positions of the radiopaque markers in x-ray projection images captured by the radiographic detector.

2. The system of claim 1, wherein the processor is further programmed to reconstruct a volume image according to the acquired projection images.

3. The system of claim 1, wherein the x-ray sources are arranged in a linear or curvilinear pattern.

4. The system of claim 1, wherein the x-ray sources are arranged in a geometric pattern shaped as a rectangle, circle, cross or triangle.

5. The system of claim 1, wherein the plurality of x-ray sources are fixed in position relative to each other.

6. The system of claim 1, wherein one or more of the radiopaque markers are fixed in position relative to one or more of the x-ray sources.

7. The system of claim 6, wherein the radiopaque markers are fixed in position relative to each other.

8. The system of claim 7, wherein the radiopaque markers are secured in a fixed position relative to each other by a radiolucent support member.

9. The system of claim 8, wherein the radiolucent support member is made from glass.

10. The system of claim 9, wherein the radiolucent support member is secured in a fixed position relative to one or more of the x-ray sources during image exposure.

11. The system of claim 8, wherein the radiolucent support member is secured in the fixed position by a rigid arm connected to the support member and to a tube head containing the one or more x-ray sources.

12. The system of claim 8, wherein the radiolucent support member is secured in the fixed position by a rigid arm connected to the support member and to any one of a floor, a ceiling, a wall and a mobile cart.

13. The system of claim 1, wherein one or more of the x-ray sources are movable to acquire one or more of the acquired projection images at a different acquisition angle.

14. The system of claim 1, wherein two or more of the x-ray sources are sealed within a single vacuum chamber.

15. The system of claim 1, wherein the processor is further programmed to digitally remove the radiopaque markers from the acquired projection images or from the reconstructed volume image.

16. The system of claim 1, wherein the radiopaque markers are each shaped as a sphere, ellipse, cylinder, cross, cube, donut, or a combination thereof.

17. The system of claim 1, wherein at least three of the radiopaque markers are disposed in each of the radiation paths during image exposure.

18. The system of claim 1, wherein each of the radiation paths includes no radiopaque markers or at least three radiopaque markers during image exposure.

19. The system of claim 1, wherein the radiopaque markers are positioned such that a different subset of the plurality of radiopaque markers are disposed in each radiation path from each of the plurality of x-ray sources during image exposure.

* * * * *